United States Patent
Yu (10) Patent No.: US 9,546,988 B2
(45) Date of Patent: Jan. 17, 2017

(54) PULSED ION MULTIFUNCTIONAL DETECTOR FOR BOTH HIGH PERFORMANCE LIQUID CHROMATOGRAPH AND ION CHROMATOGRAPH

(71) Applicants: Jiade Yu, Shanghai (CN); Chingchuen Chan, Hong Kong (CN); Qing Lu, Wuhan, Hubei Province (CN)

(72) Inventor: Jiade Yu, Shanghai (CN)

(73) Assignees: Jiade Yu, Shanghai (CN); Chingchuen Chan, Hong Kong (CN); Qing Lu, Wuchang, Wuhan, Hubei Province (CN)

( * ) Notice: Subject to any disclaimer, the term of this patent is extended or adjusted under 35 U.S.C. 154(b) by 412 days.

(21) Appl. No.: 14/287,055

(22) Filed: May 25, 2014

(65) Prior Publication Data
US 2014/0250984 A1    Sep. 11, 2014

(51) Int. Cl.
*G01N 30/96*    (2006.01)
*G01N 30/64*    (2006.01)
*G01N 30/62*    (2006.01)

(52) U.S. Cl.
CPC .............. *G01N 30/64* (2013.01); *G01N 30/96* (2013.01); *G01N 2030/626* (2013.01)

(58) Field of Classification Search
None
See application file for complete search history.

*Primary Examiner* — Laura Martin
*Assistant Examiner* — Alex Devito
(74) *Attorney, Agent, or Firm* — Tianhua Gu; Global IP Services (57) ABSTRACT

A pulsed ion multifunctional detector used for both high performance liquid chromatograph and ion chromatograph, and experiment chromatograms attached also show that the detector has excellent multipurpose function in liquid chromatograph. The casing of the instrument is provided with a sample solution inlet, a sample solution outlet, a power supply socket, a liquid crystal display, an operation keyboard and a detection signal output interface. In the casing is provided a detection electromechanical member, which includes a central controller, a detection cell, a preposed subtracting module, a polarity transformation module, a noise processing module and an output amplifier module. The pulsed ion multifunctional detector can sensitively and accurately measure ion current of sample ionized directly in the detection cell, and subtract baseline background generated by various mobile phases and automatically eliminate dynamic noise and drift of the instrument.

8 Claims, 7 Drawing Sheets

PULSED ION MULTIFUNCTIONAL DETECTOR FOR BOTH HIGH PERFORMANCE LIQUID CHROMATOGRAPH AND ION CHROMATOGRAPH

BACKGROUND OF THE PRESENT INVENTION

Field of Invention

The present invention relates to an innovative analyzing and detecting instrument, and particularly to a pulsed ion multifunctional detector for both high performance liquid chromatograph and ion chromatograph, and having excellent multipurpose function in liquid chromatograph.

Description of Related Arts

Liquid chromatograph is an instrument for detecting and analyzing a sample qualitatively and quantificationally, and is widely used in food, medicine, water quality, beverage, biochemical and health products to detect and analyze the component of the sample. At present, liquid chromatograph mainly has high performance liquid chromatograph, ion chromatograph, capillary chromatograph, gel chromatograph and the like, wherein the high performance liquid chromatograph (HPLC) and the ion chromatograph (IC) are most widely used.

Liquid chromatograph and ion chromatograph mainly include a high pressure infusion pump, a high pressure sampling system, a chromatographic column, a detector and a data processing system. Developers and users all know that during the analyzing and detecting process, firstly various mobile phases should be mixed, stirred and degassed, then the sample is prepared into a sample solution, and entered into the high pressure sampling system and delivered into the chromatographic column through the high pressure infusion pump. Since each component of the sample solution has different partition coefficient in two phases, after several times of absorption-desorption partition process, the sample can be separated, as per different time passing the chromatographic column, into individual component, which flowed out in turn from the chromatograph column and entered directly into the detector. In the detector, the concentration of the individual component of the sample is converted to voltage signal output. The data processing system is connected with a computer and performs data processing on the output electric signals, and shows the analysis result of the individual component of the sample in the form of spectrogram. From the above content, the detector is one of the most core components of the whole chromatograph. The technical performance of the detector directly decides the technical performance of the whole chromatograph and is an important prerequisite of the accurately qualitative and quantitative analysis of the sample.

In the prior art, the detector of the high performance liquid chromatograph only has self-detection function. It can only be used in the detection of the liquid chromatograph, rather than the detection of the ion chromatograph. For example, the common ultraviolet absorption detector has no ultraviolet absorption of the ion chromatographic sample, thus it can not be applied to the ion chromatograph. Similarly, the detector of the ion chromatograph is also difficult to be applied to the high performance liquid chromatograph. Take the common conductivity detector for the detection of the ion chromatograph as an example, the sensitivity of which is far below various detectors in the liquid chromatograph and is unable to subtract large scale baseline background of the mobile phase. Moreover, it is required to add expensive ion exchange column and also expensive additional inhibiting column in the detector and difficult to adapt to the variation of various allocation proportions of multiple mobile phases in the liquid chromatograph. As another example, the ion detector of DIONEX Company of America used for the ion chromatograph, has complicated structure due to indirect ionization and has high cost and price. As another example, an electrochemical detector of the ion chromatograph, the stability and the sensitivity of which is influenced by the chemical reaction of electrodes over time, and the electrodes of which are often need to be cleaned, and thus the detector is not convenient to use. In addition, none of those detectors is applied to the high performance liquid chromatograph. Thereby the detectors in the present liquid chromatographs have poor universality and are unable to achieve the function of multipurpose. Also, the technical difficulty that the sensitivity and the stability of the detector are conflicted with each other is difficult to overcome.

SUMMARY OF THE PRESENT INVENTION

In view of the abovementioned disadvantages in the prior art, the object of the present invention is to provide a pulsed ion multifunctional detector which has a simple structure, superior sensitivity and stability, and is more widely used and is used for both high performance liquid chromatograph and ion chromatograph.

In order to achieve the abovementioned object, the present invention provides a pulsed ion multifunctional detector for both high performance liquid chromatograph and ion chromatograph, including a casing with a power supply socket, the casing is provided with a sample solution inlet and a sample solution outlet, a control panel having an operation keyboard and a liquid crystal display, and a detection signal output interface, in the casing is further provided a detection electromechanical member, wherein the detection electromechanical member includes:

a central controller connected with the operation keyboard and the liquid crystal display of the control panel;

a detection cell being in communication with the sample solution inlet and the sample solution outlet;

a first electrode and a second electrode provided in the detection cell, being used for ionizing the solution in the detection cell, and generating ion current of mobile phase before entering the sample solution into the detection cell, and generating ion current of the sample as entering the sample solution into the detection cell, the first electrode is connected with the central controller, the second electrode is connected with an input terminal of a first operational amplifier in a preposed subtracting module;

a preposed subtracting module including a first operational amplifier, whose two input terminals are respectively connected with the second electrode and the central controller, for amplifying and subtracting ion current of the mobile phase before entering the sample solution into the detection cell, and causing the voltage of the first output terminal of the first operational amplifier to be zero, and amplifying ion current of the sample as entering the sample solution into the detection cell to form voltage signal of the sample;

a polarity transformation module including a second operational amplifier, the first output terminal is connected with a fixed head of a relay, the central controller is used to control the relay for switching the first output terminal to be connected with a second in-phase input terminal or a second inverting input terminal of the second operational amplifier, such that the voltage of the second output terminal of the second operational amplifier is a positive voltage;

a noise processing module including a third operational amplifier, the third operational amplifier is connected with the central controller and the second output terminal for eliminating dynamic noise and drift of the instrument;

an output amplifier module including a fourth operational amplifier, and being connected with the central controller and a third output terminal of the third operational amplifier for automatically setting zero before entering the sample solution into the detection cell, and amplifying the voltage signal of the sample and outputting the amplified voltage signal of the sample through the detection signal output interface.

Further, the preposed subtracting module further includes a first resistance, a second resistance, a multi-turn potentiometer and a stepping motor. A first inverting input terminal of the first operational amplifier is connected with the second electrode. One end of the first resistance is connected with the first inverting input terminal, and the other end is connected with the first output terminal A first in-phase input terminal of the first operational amplifier is connected with a resistance control point of the multi-turn potentiometer through the second resistance. The multi-turn potentiometer is connected with the stepping motor. The stepping motor is driven by the central controller.

Preferably, the first operational amplifier is a high impedance operational amplifier.

Further, the polarity transformation module further includes a third resistance, a fourth resistance, a fifth resistance and a first capacitor. A second inverting input terminal of the second operational amplifier is connected with the third resistance. A second in-phase input terminal of the second operational amplifier is connected with the fourth resistance. The central controller controls the relay to be connected with the third resistance or the fourth resistance. One end of the fifth resistance is connected with the second inverting input terminal and the other end is connected with the second output terminal The first capacitor is in parallel with the fifth resistance.

Further, the noise processing module further includes a sixth resistance, a seventh resistance, an eighth resistance and a second capacitor. A third inverting input terminal of the third operational amplifier is connected with the second output terminal through the sixth resistance. A third in-phase terminal of the third operational amplifier is earthed. The third output terminal of the third operational amplifier is connected with the output amplifier module. The second output terminal is connected with the central controller, and the central controller is connected with the third inverting input terminal through the seventh resistance. One end of the eighth resistance is connected with the third inverting input terminal, and the other end is connected with the third output terminal The second capacitor is in parallel with the eighth resistance.

Further, the output amplifier module further includes a ninth resistance, a tenth resistance, an eleventh resistance and a third capacitor. A fourth inverting input terminal of the fourth operational amplifier is connected with the third output terminal of the third operational amplifier through the ninth resistance. A fourth in-phase input terminal of the fourth operational amplifier is earthed. A fourth output terminal of the fourth operational amplifier is connected with the detection signal output interface. The third output terminal of the third operational amplifier is connected with the central controller and the central controller is connected with the fourth inverting input terminal through the tenth resistance. One end of the eleventh resistance is connected with the fourth inverting input terminal and the other end is connected with the fourth output terminal The third capacitor is in parallel with the eleventh resistance.

Preferably, the first electrode and the second electrode are gilded.

With the above arrangement and technical processing, the pulsed ion multifunctional detector for both high performance liquid chromatograph and ion chromatograph of the present invention has the following distinct characteristics:

In this invention, two innovative technologies are employed. Firstly, large scale baseline background of the instrument generated by various mobile phases are automatically subtracted and thus the instrument can be adapted to various allocation proportions of mobile phases, and guaranteed to work stably both in high performance liquid chromatograph and ion chromatograph. On the other hand, dynamic noise of the instrument can be automatically eliminated and meanwhile drift can be reduced. Only these two technologies are employed, can the sensitivity, the stability and the performance to price ratio be largely improved, thus the technical difficulty of objective contradiction between the sensitivity and the stability can be better overcome, which finally ensures that the sample components can be sensitively and accurately detected. Therefore, the invention can not only be applied in high performance liquid chromatograph but also in ion chromatograph, which extends the range of application of the detector effectively.

DESCRIPTION OF THE REFERENCE NUMERICAL OF THE ELEMENTS 1 power supply socket
2 casing
21 sample solution inlet
22 sample solution outlet
23 detection signal output interface
3 control panel
31 operation keyboard
32 liquid crystal display
4 detection electromechanical member
41 central controller
42 detection cell
43 first electrode
44 second electrode
45 preposed subtracting module
46 polarity transformation module
47 noise processing module
48 output amplifier module
5 first operational amplifier
51 first inverting input terminal
52 first in-phase input terminal
53 first output terminal
6 second operational amplifier
61 second inverting input terminal
62 second in-phase input terminal
63 second output terminal 7 third operational amplifier
71 third inverting input terminal
72 third in-phase input terminal
73 third output terminal
8 fourth operational amplifier
81 fourth inverting input terminal
82 fourth in-phase input terminal
83 fourth output terminal
9 relay J
10 multi-turn potentiometer W
11 stepping motor M

DETAILED DESCRIPTION OF THE PREFERRED EMBODIMENTS

In the following text, the invention will be explained in an exemplary fashion on the basis of specific embodiments.

It should be understood that the form, the scale, the size and the like shown in the drawings attached in this specification are all simply used to match with the content exposed by the specification for the skilled in the art understanding and reading, but not used to limit qualifications when the invention may be implemented. Meanwhile, terms such as "up", "down", "left", "right" and the like cited in this specification are also simply for clearness of the description but not used to limit the scope implemented by the invention. The change or the adjustment of the relative relation should also be seen as the scope of the invention when there is no substantial alteration in the technical content.

Figure 1:
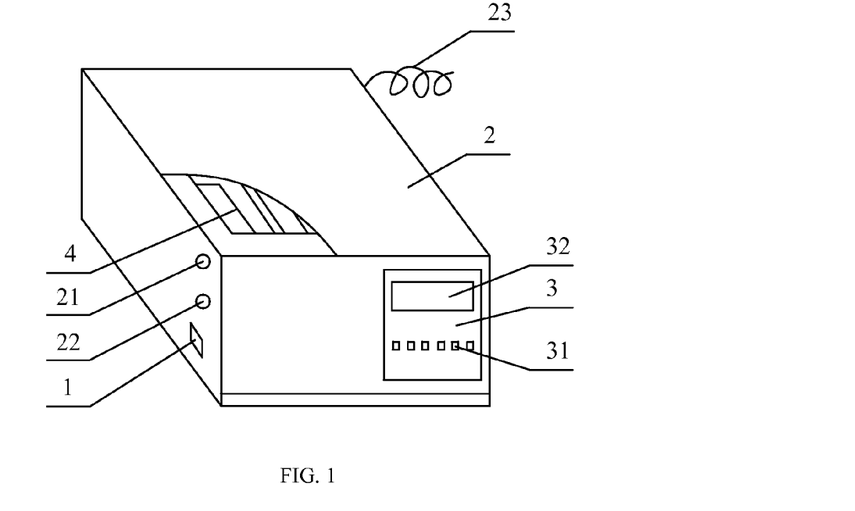
FIG. 1 is a structural diagram of the present invention.
Figure 2:
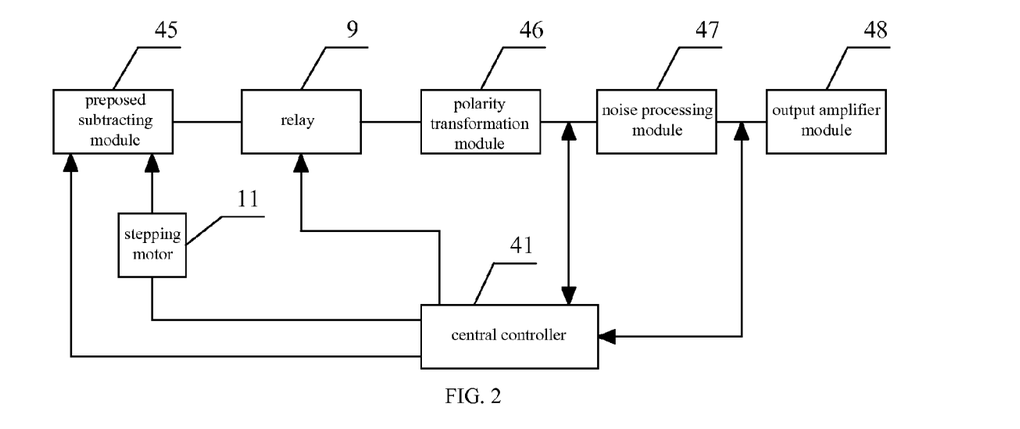
FIG. 2 is an electrical schematic diagram of a detection electromechanical member of the present invention.

As shown in FIG. 1, the invention provides a pulsed ion multifunctional detector for both high performance liquid chromatograph and ion chromatograph. The pulsed ion multifunctional detector includes a casing 2 provided with a power supply socket 1. The casing 2 is provided with a sample solution inlet 21, a sample solution outlet 22, a control panel 3 provided with an operation keyboard 31 and a liquid crystal display 32, and a detection signal output interface 23. The liquid crystal display 32 is used for tracing and displaying the working state of the detector, and facilitates to know whether the detector works normally through observation, further to determine whether the operation of the operation keyboard 31 is needed. When the pulsed ion multifunctional detector is inserted in the chromatograph, the sample solution inlet 21 is in communication with the outlet of the chromatographic column of the chromatograph or outlets connected with other detectors in series. The detection signal output interface 23 is connected with a chromatograph data processing system and a computer. The casing 2 is further provided with a detection electromechanical member 4, which is used for detecting the components of the sample. The detection electromechanical member 4 includes:

a central controller 41 composed of a microcomputer and connected with the operation keyboard 31 and the liquid crystal display 32 of the control panel 3;

a detection cell 42 being in communication with the sample solution inlet 21 and the sample solution outlet 22;

a first electrode 43 and a second electrode 44 provided in the detection cell 42, wherein the first electrode 43 is applied with a pulse voltage by the central controller 41, which can ionize the mobile phase or the sample solution in the detection cell 42 into ion current. Only ion current of the mobile phase is generated before the sample solution is entered into the detection cell 42, such electric signal is the baseline background of the instrument, and the baseline background is subtracted in the preposed subtracting module. Ion current of the sample expected to be detected is generated when the sample solution is entered into the detection cell 42;

a preposed subtracting module 45, including a first operational amplifier 5 whose two input terminals are respectively connected with the second electrode 44 and the central controller 45, and used for subtracting the ion current of the mobile phase before the sample solution entering into the detection cell 42 and causing the voltage of the first output terminal 53 of the first operational amplifier 5 to be zero to subtract the baseline background of the instrument generated by the mobile phases, which makes the baseline of the instrument close to zero line and thereby a large scale zero setting is achieved before the entry of the sample solution, and meanwhile amplifies ion current of the sample when the sample solution is entered into the detection cell and forms voltage signal of the sample;

a polarity transformation module 46, including a second operational amplifier 6, wherein the first output terminal 53 is connected with a fixed head of a relay 9, the central controller is used to control the working state of the relay by setting two switch positions: the first output terminal 53 is connected with a inverting input terminal 61 of the second operational amplifier 6 or connected with a in-phase input terminal 62 of the second operational amplifier 6, so as to achieve the voltage polarity transformation and ensure the voltage of a output terminal 63 of the second operational amplifier 6 to be positive;

a noise processing module 47, including a third operational amplifier 7, wherein the central controller is connected with the second output terminal 63 for the randomly reading and depositing of mobile phases and dynamic noise and drift generated by previous stage circuit module, to achieve a random automatic trace before and after the detection of the sample and an entry into the third operational amplifier 7 in the form of reversed phase electric signal, to eliminate the dynamic noise and drift of the instrument;

an output amplifier module 48, including a fourth operational amplifier 8, wherein the central controller 41 is connected with the third output terminal 73 for amplifying the voltage signal of the sample and automatically setting zero. The automatic zero setting is implemented as needed before the entry of the sample solution (mobile phases are only entered). The detection signal output interface 23 only outputs the amplified voltage signal of the sample and may deliver the amplified voltage signal to the chromatograph data processing system. Finally the electric signal of the sample and the detection results of each component of the sample solution are shown and stored in the form of chromatogram in the computer.

The pulsed ion multifunctional detector can sensitively and accurately measure ion current signal of the sample, automatically subtract the baseline background of the instrument generated by various mobile phases, and can automatically eliminate dynamic noise and drift of the instrument, thereby the sensitivity, stability and performance to price ratio of the instrument are significantly improved and finally the detection of the components of the sample is ensured to be sensitive and accurate. In addition, the pulsed ion multifunctional detector is adapted to various allocation proportions of the mobile phases, hence can be applied both in high performance liquid chromatograph and ion chromatograph, and further extends the range of application of the detector effectively. On the other hand, in the present embodiment, that the detection cell 42 has a small volume with the first electrode 43 and the second electrode 44 gilded guarantees for the directly and rapidly ionizing of the components of the sample, and the low cost of the instrument. The detection cell 42 is stable for long-term use without frequently wash, and the resolution of the instrument on the components of the sample is improved.

In this application, the control panel 3 is further provided with the liquid crystal display 32, which facilitates an automatic monitoring of various normal working states of the instrument. The operation keyboard 31 includes a plurality of operation keys. The plurality of operation keys are respectively used to control the operation of the instrument: a key of subtracting the baseline background, a key of polarity transformation, a key of noise processing, a key of sensitivity stepper and a key of automatically zero set. There is an alphabetic character marked on each of the plurality of operation keys. After the detector inserted in the chromatograph, firstly the power supplies of the high pressure infusion pump and the detector turn on, then the high pressure infusion pump begins to deliver solution. As the mobile phases in the whole instrument from the chromatographic column to the detector is in a normal state of fluid flow, the detector warms up and stabilizes for a certain time, which lasts usually for one hour or so. This circumstance is a warming-up and a pending stable state of the detector before the detection of the sample. After the instrument is stable, in order to sensitively and accurately detect the sample, the detector is firstly properly adjusted as followed before the sample solution is entered: except for the key of noise processing, other four keys are adjusted once just before the sample solution is initially entered. In the case of constant analysis condition and stable instrument, the four keys are not needed to be frequently adjusted. Since small-scale dynamic drift and variable noise of the instrument are all needed to be traced and eliminated by the central controller 41 anytime, only the key of noise processing is determined whether needed to be adjusted according to the condition of voltage variation and chromatogram baseline shown in the liquid crystal display 32 or the computer before the sample is entered every time. And there is no need to adjust the key of noise processing if the instrument is in a steady and normal state. After the above four keys are properly adjusted, the preposed subtracting module 45 automatically subtracts the baseline background generated by mobile phases and automatically adjusts the instrument with a baseline position of zero. The noise processing module 47 automatically traces and eliminates dynamic noise and drift of the instrument, and maintains the steady state of the instrument. The sample solution is then entered into the high pressure sampling system of the chromatograph. The sample solution is delivered into the chromatographic column by the high pressure infusion pump and is separated in turn. The separated components are directly entered into the detection cell 42 to be ionized, thereby ion currents of the sample are generated and the detection of the sample components is achieved.

Figure 3:
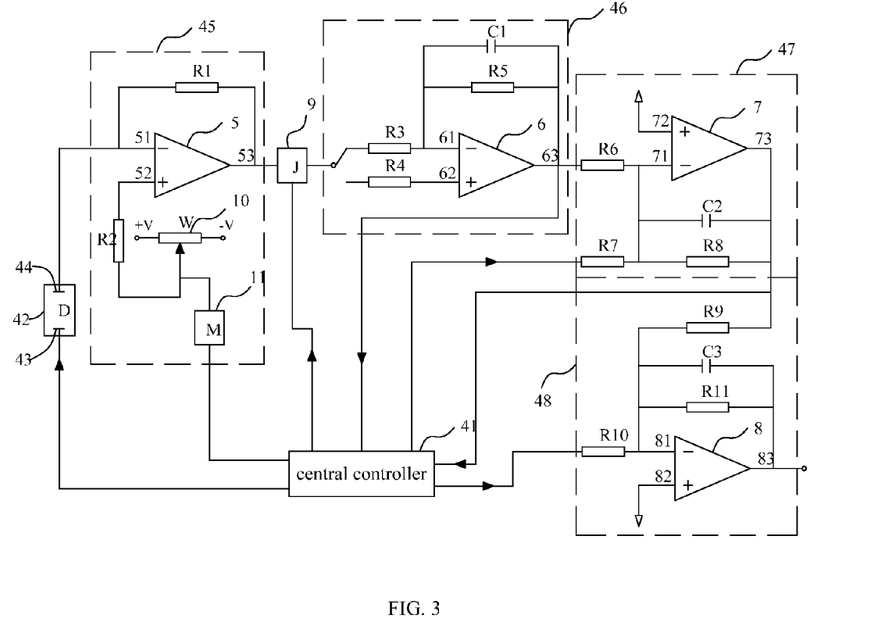
FIG. 3 is a circuit diagram of the electrical work of FIG. 2.

Specifically, as shown in FIG. 3, the preposed subtracting module 45 further includes a first resistance R1, a second resistance R2, a multi-turn potentiometer 10 and a stepping motor 11. The first inverting input terminal 51 of the first operational amplifier 5 is connected with the second electrode 44. One end of the first resistance R1 is connected with the first inverting input terminal 51 of the first operational amplifier 5, and the other end is connected with the first output terminal 53 of the first operational amplifier 5. The first in-phase input terminal 52 of the first operational amplifier 5 is connected with the resistance control point of the multi-turn potentiometer 10 through the second resistance R2. The multi-turn potentiometer 10 is connected with the stepping motor 11 and two ends of the multi-turn potentiometer 10 are applied with a positive direct voltage and a negative direct voltage. The stepping motor 11 is driven by the central controller 41.

After the enabling of preposed subtracting module and before the entering of sample solution, the solution in the detection cell 42 is just mobile phase. The first electrode 43 of the detection cell 42 is applied with a pulse voltage (generally the frequency of the pulse voltage is f=10 KC) sent out by the central controller 41, such that the mobile phase in the detection cell 42 is ionized under the action of the electric field between the first electrode 43 and the second electrode 44 and ion current I of the mobile phase is generated. The Ion current I of the mobile phase is transmitted to the first inverting input terminal 51 of the first operational amplifier 5 and is amplified by the first resistance R1. And the voltage value of the first output terminal 53 of the first operational amplifier 5 is V=I*R1. The voltage value V of the first output terminal 53 is detected by the central controller 41. After pressing the key of subtracting the baseline background, the rotation of the stepping motor 11 is driven by the central controller 41. The stepping motor 11 drives the resistance control point of the multi-turn potentiometer 10 to move, so that the multi-turn potentiometer 10 generates a direct voltage −V which is equal to the voltage value V of the first output terminal 53 with opposite polarity, and is transmitted to the in-phase input terminal 52 of the first operational amplifier 5. Therefore the voltage value V generated by the mobile phase is counteracted, which ensures the voltage of the first output terminal 53 of the first operational amplifier 5 to be zero after the instrument is stable, performs the subtracting of the baseline background generated by the mobile phase and guarantees a large scale zero setting before the sample solution is entered.

Preferably, the first operational amplifier 5 is a high impedance operational amplifier.

Further, as shown in FIG. 3, the polarity transformation module 46 further includes a third resistance R3, a fourth resistance R4, a fifth resistance R5 and a first capacitor C1. The second inverting input terminal 61 of the second operational amplifier 6 is connected with the third resistance R3. The second in-phase input terminal 62 of the second operational amplifier 6 is connected with the fourth resistance R4. The relay 9 is controlled by the central controller 41 to be connected with the third resistance R3 or the fourth resistance R4. One end of the fifth resistance R5 is connected with the second inverting input terminal 61, and the other end is connected with the second output terminal 63. The first capacitor C1 is in parallel with the fifth resistance R5. The pulse voltage transmitted by the central controller 41 to the first electrode 43 may be chosen as a positive pulse voltage or a negative pulse voltage through the key of polarity transformation. When the pulse voltage applied to the first electrode 43 is a negative pulse voltage, the output voltage of the first output terminal 53 is positive, and the relay 9 is controlled by the central controller 41 to be connected with the second in-phase input terminal 62 through the fourth resistance R4, which ensures the voltage of the second output terminal 63 to be positive. When the pulse voltage applied to the first electrode 43 is a positive pulse voltage, the output voltage of the first output terminal 53 is negative, and the relay 9 is controlled by the central controller 41 to switch, namely to be connected with the second inverting input terminal 61 through the third resistance R3, which ensures the voltage of the second output terminal 63 also to be positive. Therefore the polarity transformation of the output voltage is effectively realized through the relay 9 and the polarity transformation module 46, which guarantees the voltage of the second output terminal 63 to be positive and ensures conventional forward output and chromatogram.

Preferably, the second operational amplifier 6 is an operational amplifier with small offset voltage and current.

Further, as shown in FIG. 3, the noise processing module 47 is a comparison circuit which relies mainly on the third operational amplifier 7. The noise processing module 47 further includes a sixth resistance R6 and a seventh resistance R7. The third inverting input terminal 71 of the third operational amplifier 7 is connected with the second output terminal 63 through the sixth resistance R6. The third in-phase terminal 72 of the third operational amplifier 7 is earthed. The third output terminal 73 of the third operational amplifier 7 is connected with the output amplifier module 48. The second output terminal 63 is connected with the central controller 41 and the central controller 41 is connected with the third inverting input terminal 71 through the seventh resistance R7. After the instrument is started up and operates stably, the voltage of the second output terminal 63 includes dynamic noise and drift of the instrument generated by the mobile phase and previous stage circuit. The dynamic noise and drift of the instrument is set as Vn. The central controller 41 composed of a microcomputer randomly traces, reads and deposits the voltage of the second output terminal 63, namely the dynamic noise and drift Vn of the instrument. The central controller 41 then randomly and timely transmits the inversion signal −Vn to the third inverting input terminal 71 of the third operational amplifier 7 through the seventh resistor R7, to counteract the dynamic noise and drift Vn of the instrument, and achieve a small scale random zero setting to guarantee that the electric signal of the third output terminal 73 of the noise processing module 47 is particularly stable, and eliminate the noise while reduce the drift. When the sample components are entered, only a small part of the electric signal of Vn is counteracted and a large amount of the stable electric signal generated by the sample may further be amplified by the latter output amplifier module, which solves the objective technical difficulty as follows: signal-to-noise ratio has no changes since the voltage signal of the sample and the value of useless noise and drift are simultaneously amplified. Because a large amount of noise and drift are eliminated in the invention (namely the stability is improved), a better amplification may be implemented in the former and latter various modules, the sensitivity is significantly improved and the technical difficulty of objective contradiction between the sensitivity and the stability is better overcome, which finally ensures high sensitivity and stability of the instrument and accuracy of the detection result.

Preferably, as shown in FIG. 3, the noise processing module 47 further includes an eighth resistance R8 and a second capacitor C2. One end of the eighth resistance R8 is connected with the third inverting input terminal 71, and the other end is connected with the third output terminal 73. The second capacitor C2 is in parallel with the eighth resistance R8. The second capacitor C2 may eliminate high frequency noise in the voltage of the second output terminal 63.

Further, as shown in FIG. 3, the output amplifier module 48 is also a comparison circuit which relies mainly on the fourth operational amplifier 8. The output amplifier module 48 further includes a ninth resistance R9 and a tenth resistance R10. The fourth inverting input terminal 81 of the fourth operational amplifier 8 is connected with the output terminal of the noise processing module 47 through the ninth resistance R9. The fourth in-phase input terminal 82 of the fourth operational amplifier 8 is earthed. The fourth output terminal 83 of the fourth operational amplifier 8 is connected with the detection signal output interface 23. The output terminal of the noise processing module 47 is connected with the central controller 41 and the central controller 41 is connected with the fourth inverting input terminal 81 through the tenth resistance R10 to implement automatic zero setting of the output amplifier module 48. The output amplifier module 48 is not necessary to be set to zero before the instrument is stable. Once pressing the key of automatically setting zero on the operation keyboard before the sample solution is entered, the central controller 41 automatically performs zero setting on the output amplifier module 48 responding to the pressing of the key. When the output amplifier module 48 is automatically set to zero, the central controller 41 detects the electric signal Vc of the third output terminal 73 of the noise processing module 47 and transmits the inversion signal −Vc to the inverting input terminal of the fourth operational amplifier 8 through the tenth resistance R10, to counteract the electric signal Vc of the third output terminal 73, and achieve an automatic zero setting before the sample is entered. The amplifying of the output amplifier module 48 depends on the selection of the ninth resistance R9, the tenth resistance R10 and the eleventh resistance R11. Generally, the ninth resistance R9 is chosen to be equal to the tenth resistance R10 and the ratio of the eleventh resistance R11 to the ninth resistance R9 is amplification factor. Finally the fourth output terminal 83 of the output amplifier module 48 generates a high sensitive and high stability detection signal of the sample, and the detection signal of the sample is transmitted to the detection signal output interface 23.

Preferably, the output amplifier module 48 further includes an eleventh resistance R11 and a third capacitor C3. One end of the eleventh resistance R11 is connected with the fourth inverting input terminal 81 and the other end is connected with the fourth output terminal 83. The third capacitor C3 is in parallel with the eleventh resistance R11 and may eliminate high frequency noise of the voltage of the third output terminal 73.

In summary, the pulsed ion multifunctional detector of the invention may be applied in both high performance liquid chromatograph and ion chromatograph, and achieve the function of multipurpose well. Since the large scale baseline background of the instrument is automatically subtracted, the instrument can adapt to various allocation proportions of various mobile phases, and guarantees a normal operation state. In addition, the invention employs a dual technology of automatic elimination of dynamic noise and reduction of drift of the instrument, which significantly improves the sensitivity and stability of the instrument, and ensures the instrument with distinct technical advancement, economical efficiency and utility.

Figure 4:
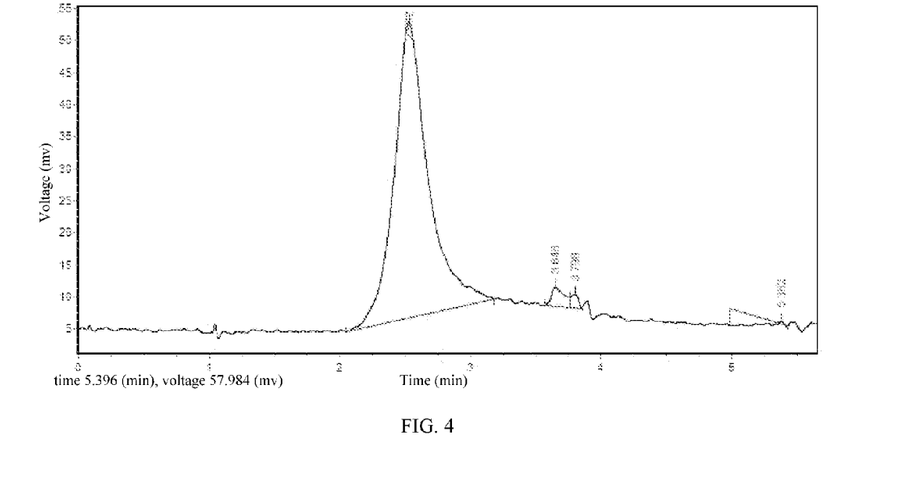
FIGS. 4-13 are chromatograms obtained by using the detector to detect the components of a sample.

Embodiments in which the invention is used to detect different sample components are listed:

First Embodiment the pulsed ion multifunctional detector is applied in a liquid chromatograph detection sample: glycerin (standard detection sample of differential refraction detector)

detection environment: chromatographic column: C18, ODS; flow velocity: 0.6 ml/min; mobile phase: 100% methyl alcohol chromatogram obtained after the detection is as shown in FIG. 4.

Figure 5:
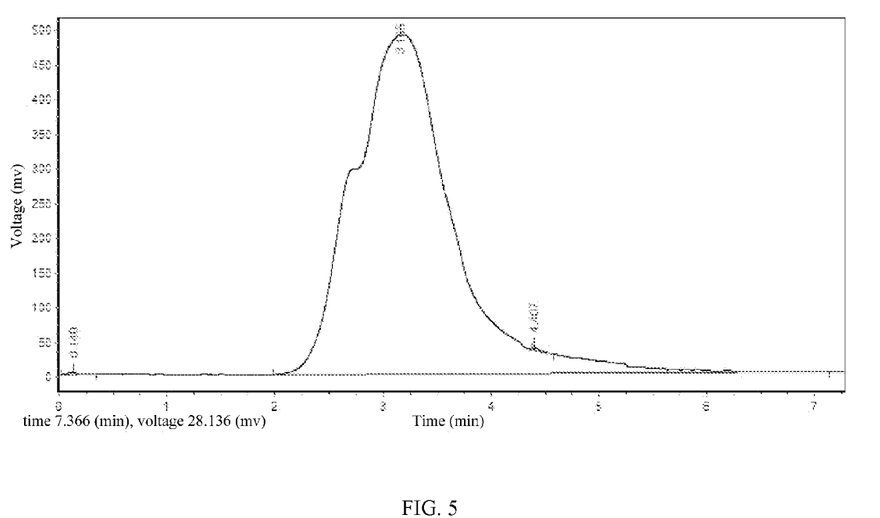

Second Embodiment the pulsed ion multifunctional detector is applied in a liquid chromatograph
detection sample: nongfuspring pure water
detection environment: chromatographic column: C18, ODS; flow velocity: 0.6 ml/min; mobile phase: 100% methyl alcohol
chromatogram obtained after the detection is as shown in FIG. 5.

Figure 6:
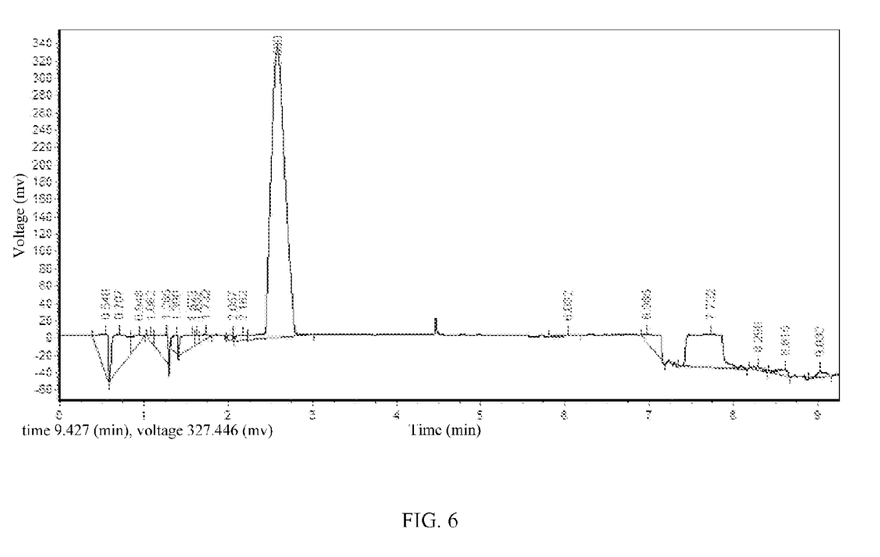

Third Embodiment the pulsed ion multifunctional detector is applied in a liquid chromatograph
detection sample: Noni fruit juice (American health product)
detection environment: chromatographic column: C18, ODS; flow velocity: 0.6 ml/min; mobile phase: 100% methyl alcohol
chromatogram obtained after the detection is as shown in FIG. 6.

Figure 7:
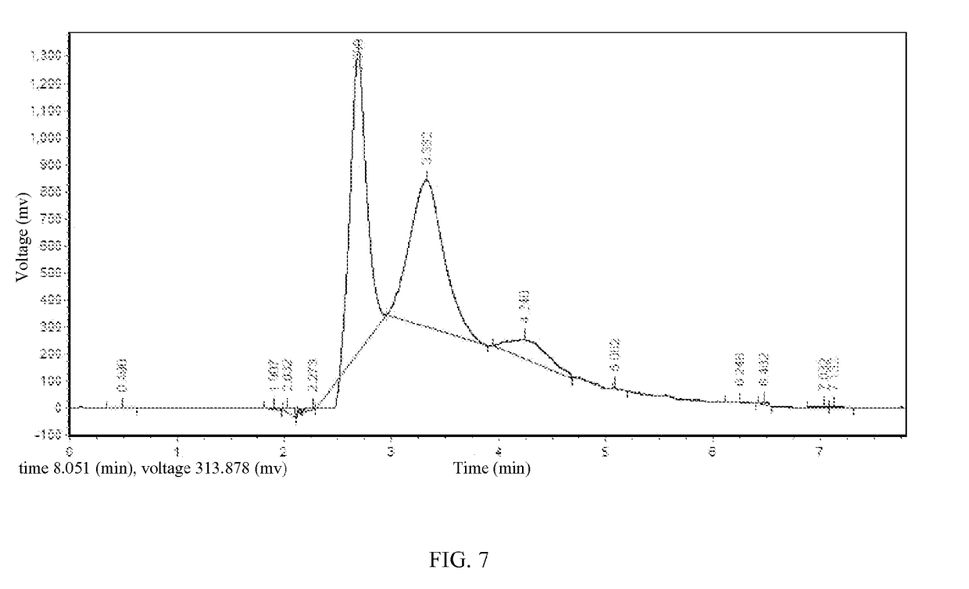

Fourth Embodiment the pulsed ion multifunctional detector is applied in a liquid chromatograph
detection sample: lactic acid bacteria (American health product)
detection environment: chromatographic column: C18, ODS; flow velocity: 0.6 ml/min; mobile phase: 100% methyl alcohol
chromatogram obtained after the detection is as shown in FIG. 7.

Figure 8:
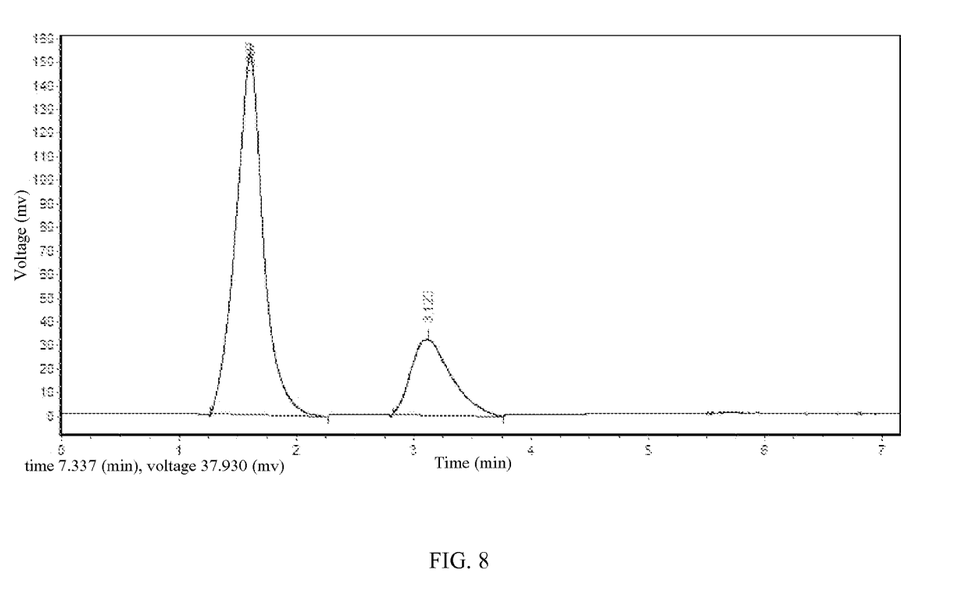

Fifth Embodiment the pulsed ion multifunctional detector is applied in a liquid chromatograph
detection sample: dietary alkali
detection environment: chromatographic column: C18, ODS; flow velocity: 0.6 ml/min; mobile phase: 100% methyl alcohol
chromatogram obtained after the detection is as shown in FIG. 8.

Figure 9:
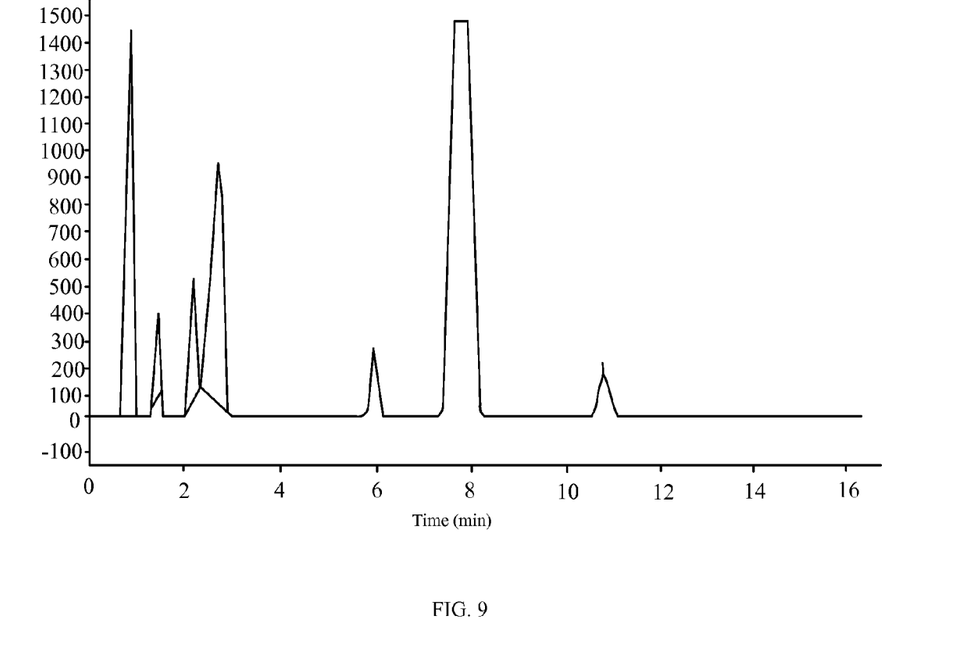

Sixth Embodiment the pulsed ion multifunctional detector is applied in a ion chromatograph
detection sample: standard detection sample of ion chromatograph
detection environment: ion column; flow velocity: 1 ml/min; mobile phase: water, sodium bicarbonate, sodium carbonate
Chromatogram obtained after the detection is as shown in FIG. 9. As shown in FIG. 9, there are totally 7 spectral peaks from left to right by which components are respectively represented as $Cl^-$, $NO_2^-$, $Br^-$, $NO_3^-$, $PO_4^{3-}$, $SO_4^{2-}$ and oxalate.

Figure 10:
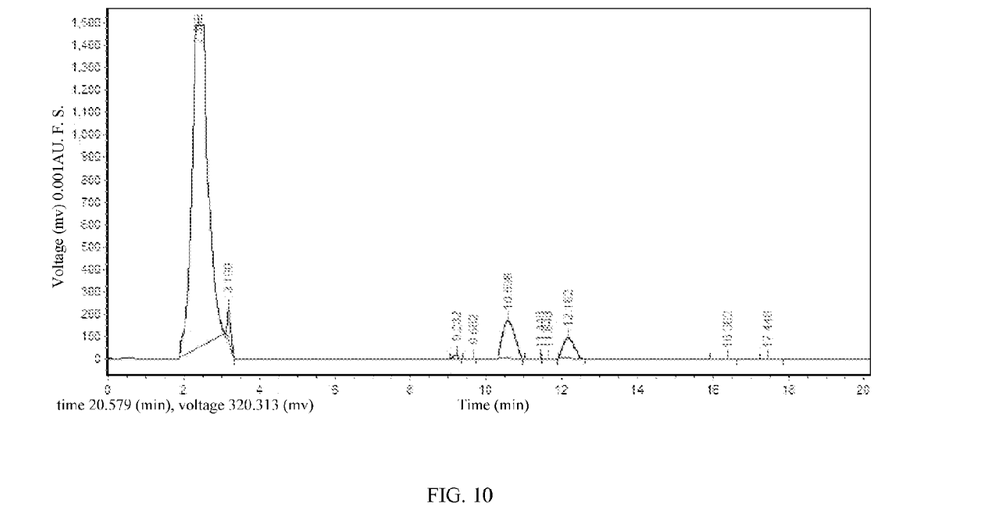

Seventh Embodiment the pulsed ion multifunctional detector is applied in a liquid chromatograph
detection sample: linolenic acid gelatin pearl (medicine for healing cerebral thrombosis)
detection environment: chromatographic column: C18, ODS; flow velocity: 0.6 ml/min; mobile phase: 100% methyl alcohol
chromatogram obtained after the detection is as shown in FIG. 10.

Figure 11:
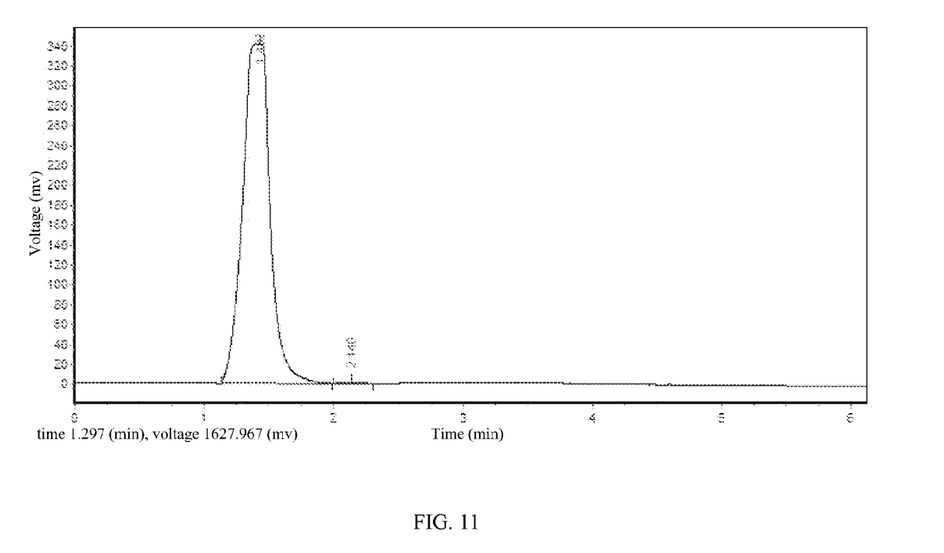

Eighth Embodiment the pulsed ion multifunctional detector is applied in a liquid chromatograph
detection sample: table salt
detection environment: chromatographic column: C18, ODS; flow velocity: 0.6 ml/min; mobile phase: 100% methyl alcohol
chromatogram obtained after the detection is as shown in FIG. 11.

Figure 12:
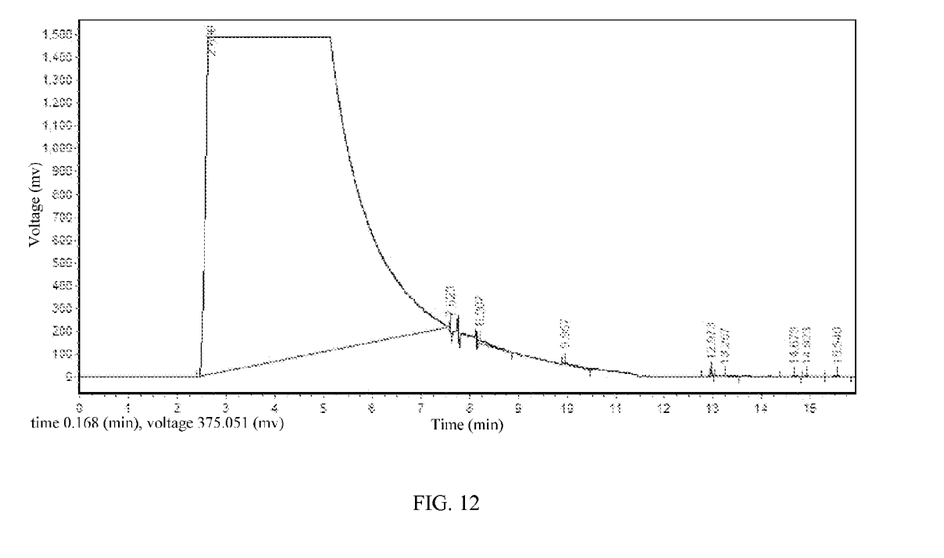

Ninth Embodiment the pulsed ion multifunctional detector is applied in a liquid chromatograph
detection sample: quinine sulfate and perchloric acid solution (standard detection sample of fluorescence detector)
detection environment: chromatographic column: C18, ODS; flow velocity: 0.6 ml/min; mobile phase: 100% methyl alcohol
chromatogram obtained after the detection is as shown in FIG. 12.

Figure 13:
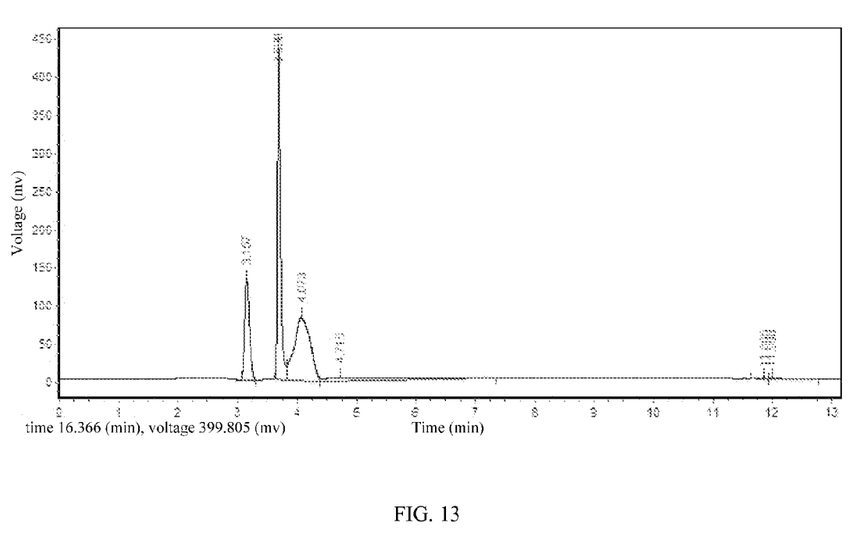

Tenth Embodiment the pulsed ion multifunctional detector is applied in a liquid chromatograph
detection sample: pentacene
detection environment: chromatographic column: C18, ODS; flow velocity: 0.6 ml/min; mobile phase: 100% methyl alcohol
chromatogram obtained after the detection is as shown in FIG. 13

From the above 10 chromatograms, it is known that the pulsed ion multifunctional detector of the invention is used in both high performance liquid chromatograph and ion chromatograph, and it is proved that the liquid chromatography also has detection functions of other detectors and also has excellent multipurpose function and has good detection sensitivity and stability. Therefore, the present invention overcomes the drawbacks in the prior art and has high industrial utilization value and provides a new multifunctional instrument for analyzing and detecting.

The above embodiments simply schematically illustrate principle and effect of the invention. There are more experiments to be performed except the above embodiments. The product of the invention is also in series with a ultraviolet detector of the high performance liquid chromatograph and an electrical conductivity detector of the ion chromatograph to perform an experiment: comparing detection ability and performance difference between the invention and other detectors and storing the comparison chromatogram.

What is claimed is:
1. A pulsed ion multifunctional detector for both high performance liquid chromatograph and ion chromatograph, including a casing with a power supply socket, the casing is provided with a sample solution inlet, a sample solution outlet, a control panel with an operation keyboard and a liquid crystal display, and a detection signal output interface, in the casing is further provided a detection electromechanical member, characterized in that: the detection electromechanical member includes:

a central controller connected with the operation keyboard and the liquid crystal display of the control panel;

a detection cell being in communication with the sample solution inlet and the sample solution outlet;

a first electrode and a second electrode provided in the detection cell, the first electrode is connected with the central controller for ionizing solution in the detection cell, and generating ion current of mobile phase before entering sample solution into the detection cell and generating ion current of sample as entering sample solution into the detection cell;

a preposed subtracting module including a first operational amplifier, whose two input terminals are respectively connected with the second electrode and the central controller, for amplifying and subtracting ion current of mobile phase before entering sample solution into the detection cell, and causing the voltage of the first output terminal of the first operational amplifier to be zero, and amplifying ion current of sample as entering sample solution into the detection cell to form voltage signal of sample;

a polarity transformation module including a second operational amplifier, the first output terminal is connected with a fixed head of a relay, the central controller is used to control the relay for switching the first output terminal to be connected with a second in-phase input terminal or a second inverting input terminal of the second operational amplifier, such that the voltage of the second output terminal of the second operational amplifier is a positive voltage;

a noise processing module including a third operational amplifier, the third operational amplifier is connected with the central controller and the second output terminal for eliminating dynamic noise and drift of the instrument;

an output amplifier module including a fourth operational amplifier, and being connected with the central controller and a third output terminal of the third operational amplifier for automatically setting zero before entering sample solution into the detection cell, amplifying the voltage signal of sample and outputting the amplified voltage signal of sample through the detection signal output interface.

2. The pulsed ion multifunctional detector according to claim 1, characterized in that: the preposed subtracting module further includes a first resistance, a second resistance, a multi-turn potentiometer and a stepping motor, a first inverting input terminal of the first operational amplifier is connected with the second electrode, one end of the first resistance is connected with the first inverting input terminal, and the other end is connected with the first output terminal, a first in-phase input terminal of the first operational amplifier is connected with a resistance control point of the multi-turn potentiometer through the second resistance, the multi-turn potentiometer is connected with the stepping motor, and the stepping motor is driven by the central controller.

3. The pulsed ion multifunctional detector according to claims 1, characterized in that: the first operational amplifier is a high impedance operational amplifier.

4. The pulsed ion multifunctional detector according to claim 1, characterized in that: the polarity transformation module further includes a third resistance, a fourth resistance, a fifth resistance and a first capacitor, a second inverting input terminal of the second operational amplifier is connected with the third resistance, a second in-phase input terminal of the second operational amplifier is connected with the fourth resistance, the central controller controls the relay to be connected with the third resistance or the fourth resistance, one end of the fifth resistance is connected with the second inverting input terminal, and the other end is connected with the second output terminal, the first capacitor is in parallel with the fifth resistance.

5. The pulsed ion multifunctional detector according to claim 1, characterized in that: the noise processing module further includes a sixth resistance, a seventh resistance, an eighth resistance and a second capacitor, a third inverting input terminal of the third operational amplifier is connected with the second output terminal through the sixth resistance, a third in-phase terminal of the third operational amplifier is earthed, the third output terminal of the third operational amplifier is connected with the output amplifier module, the second output terminal is connected with the central controller, and the central controller is connected with the third inverting input terminal through the seventh resistance, one end of the eighth resistance is connected with the third inverting input terminal, and the other end is connected with the third output terminal, the second capacitor is in parallel with the eighth resistance.

6. The pulsed ion multifunctional detector according to claim 1, characterized in that: the output amplifier module further includes a ninth resistance, a tenth resistance, an eleventh resistance and a third capacitor, a fourth inverting input terminal of the fourth operational amplifier is connected with the third output terminal of the third operational amplifier through the ninth resistance, a fourth in-phase input terminal of the fourth operational amplifier is earthed, a fourth output terminal of the fourth operational amplifier is connected with the detection signal output interface, the third output terminal of the third operational amplifier is connected with the central controller, and the central controller is connected with the fourth inverting input terminal through the tenth resistance, one end of the eleventh resistance is connected with the fourth inverting input terminal, and the other end is connected with the fourth output terminal, the third capacitor is in parallel with the eleventh resistance.

7. The pulsed ion multifunctional detector according to claim 1, characterized in that: the first electrode and the second electrode are gilded.

8. The pulsed ion multifunctional detector according to claims 2, characterized in that: the first operational amplifier is a high impedance operational amplifier.

* * * * *